United States Patent [19]

Plonka et al.

[11] B 4,001,293

[45] Jan. 4, 1977

[54] PROCESS FOR PRODUCTION OF γ-HALONITRILES

[75] Inventors: James H. Plonka; Ralph A. Davis, both of Midland, Mich.

[73] Assignee: The Dow Chemical Company, Midland, Mich.

[22] Filed: Apr. 2, 1975

[21] Appl. No.: 564,252

[44] Published under the second Trial Voluntary Protest Program on March 2, 1976 as document No. B 564,252.

[52] U.S. Cl. .................. 260/465.7; 260/465.8 R
[51] Int. Cl.² ............................................. C07C 120/04
[58] Field of Search ............................ 260/465.7

[56] References Cited

UNITED STATES PATENTS

| | | | |
|---|---|---|---|
| 2,415,261 | 2/1947 | Rogers | 260/465.7 X |
| 2,800,497 | 7/1957 | Indest | 260/465.7 |
| 3,725,458 | 4/1973 | Starks | 260/465.3 X |
| 3,839,399 | 10/1974 | Starks et al. | 260/465.1 X |

OTHER PUBLICATIONS

Starks, J.A.C.S., 93, 1971, pp. 195–199.
Allen, Organic Synthesis, Coll. vol. I, 2nd ed., 1941, pp. 156–157.
Starks, J.A.C.S., 95, 1973, pp. 3613–3617.
Rappoport, "The Chemistry of the Cyano Group," 1970, pp. 77–79, Interscience Publishers.

*Primary Examiner*—Joseph P. Brust
*Attorney, Agent, or Firm*—G. R. Plotecher; R. M. Mellom

[57] ABSTRACT

A new process for preparing γ-halonitriles comprising reacting by contacting a 1,3-dihalopropane, such as 1-chloro-3-bromopropane, or mixtures thereof, such as 1-chloro-3-bromopropane and 1-chloro-3-iodopropane, with an alkali metal cyanide, such a sodium cyanide, in the presence of an onium salt, such as benzyltriethylammonium chloride, and an alkali metal halide, such as sodium chloride. The γ-halonitriles are useful in preparing cyclopropylcyanide, a herbicide intermediate.

14 Claims, No Drawings

PROCESS FOR PRODUCTION OF γ-HALONITRILES

This invention relates to the art of preparing γ-halonitriles. In one aspect, the invention is directed to processes for preparing γ-halobutylnitriles. In another aspect, the invention is directed to processes for preparing γ-halobutylnitriles by means of an onium salt catalyst. In still another aspect, the invention is directed to processes for preparing γ-halobutylnitriles in the presence of an alkali metal halide by means of an onium salt catalyst.

BACKGROUND OF THE INVENTION

Processes for preparing γ-halonitriles are replete in the art. For example, it has long been known that γ-chlorobutylnitrile can be prepared by heating potassium cyanide in a water-ethanol solution with 1-chloro-3-bromo-propane. Organic Synthesis 8, 52–3 (1928). More recently, patents have issued that employ catalysis to facilitate γ-halonitrile formation. Illustrative is Horrom (U.S. Pat. No. 3,118,926) wherein thionyl chloride and γ-hydroxybutylamide were reacted under reflux conditions for 16 hours in the presence of a catalytic amount of pyridine. The art does not disclose the use of an onium salt catalyst in the preparation of γ-halonitriles, although Erickson (U.S. Pat. No. 2,524,011) teaches the use of said catalyst in the preparation of β-chloro-isobutylnitrile from hydrogen chloride and methacrylonitrile.

These teachings suffer from a number of deficiencies. Yields are generally low, some require the use of organic solvents, and others are hampered by large dinitrile formation. These deficiencies result in inefficient use of source material and require complicated, time consuming recovery techniques. In turn, waste problems and increased labor and capital costs are incurred.

STATEMENT OF THE INVENTION

According to this invention, these and other deficiencies of the prior art are overcome by a process for preparing γ-halonitriles which comprises reacting by contacting a 1,3-dihalopropane or mixtures thereof, with an alkali metal cyanide in the presence of an onium salt and an alkali metal halide. The features of the invention which produce the improved results include the combination of a phase transfer catalyst and an alkali metal halide. The phase transfer catalyst, in the form of an onium salt, serves to both accelerate the reaction and eliminate the need for an organic solvent. The alkali metal halide functions in the combination to reduce the formation of undesirable side products such as dinitriles. Consequently, the combination of phase transfer catalyst and alkali metal halide results in a reduction in reaction time, eliminates a separation step in the product recovery because there is no organic solvent present, and an increase in the γ-halonitrile yield. For example, yields have been obtained in excess of 98 percent, based on theoretical cyanide, with a desirable product distribution.

While the invention is practiced in the presence of water, only sufficient water to dissolve the inorganic salts is necessary. The invention can be practiced in the presence of an organic solvent, but for obvious economic reasons, it is preferred to practice the invention in the absence of an organic solvent.

The γ-halobutylnitriles which are obtained may be a mixture of chloro- and bromo-, both of which are useful in cyclopropylcyanide production. The dinitrile compound also produced is not useful in said production but as heretofore stated, the process of the present invention holds its formation to a minimum. Because the dinitrile compound is unreactive in the cyclopropylcyanide process, its removal from the γ-halobutylnitrile mixture is unnecessary. However, if its removal is desired, any suitable known technique can be used.

Accordingly, it is an object of this invention to provide a process of the production of γ-halonitriles wherein the formation of unwanted side-products are either reduced or eliminated.

Another object of this invention is to provide a process for the production of γ-halonitriles wherein the yield of same is maximized.

Another object of this invention is to provide a process for the production of γ-halonitriles wherein the need for an organic solvent is eliminated.

Still another object of this invention is to provide a process for the production of γ-halonitriles wherein the reaction time is minimized.

These and other objects of the invention will become apparent to one skilled in the art after studying the following detailed description and appended claims.

DETAILED DESCRIPTION OF THE INVENTION

The 1,3-dihalopropanes which are used as a source material in the practice of this invention include 1-chloro-3-bromopropane, 1-chloro-3-iodopropane, 1-bromo-3-iodopropane, 1,3-dichloropropane, 1,3-dibromopropane, 1,3-diiodopropane, and combinations thereof. 1-chloro-3-bromopropane and 1-chloro-3-iodopropane are preferred, with the former specially preferred.

Any known and suitable alkali metal cyanide can be used in the instant process but the sodium and potassium cyanides are the most familiar and therefore preferred. Mixtures of such alkali metal cyanides are acceptable.

Similarly, any known and suitable alkali metal halide can be used in the instant process. However, in deference to practical and economical constraints, sodium or potassium chloride, sodium or potassium bromide, and sodium or potassium iodide are preferred. Sodium or potassium chloride is specially preferred.

The catalysts here used are organic onium salts selected from the group consisting of a quaternary ammonium salt, a quaternary phosphonium salt, and a tertiary sulfonium salt. These salts are known in the art as phase-tranfer catalysts and are described in such publications as the J. Am. Chem. soc. 93, 195 (1971) and in British Pat. No. (1,227,144) by Starks and Napier. Said disclosures are herein incorporated by reference. The ammonium salts are preferred over the other onium salts and benzyltrimethyl-, benzyltriethyl- and tetrabutylammonium chlorides and bromides are most preferred.

To further illustrate the type of onium salts used, suitable onium salts are represented by the formula

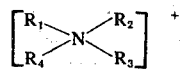

wherein $R_1$–$R_4$ are hydrocarbyl groups, i.e. alkyl, aryl, alkylaryl, arylalkyl, cycloalkyl, etc., and $R_1$ can join with $R_2$, or $R_2$ with $R_3$, etc., to form a 5- or 6-membered heterocyclic compound having at least one quaternized nitrogen atom in the ring and may also contain one atom of nitrogen, oxygen or sulfur within the ring. Typically, $R_1-R_4$ are hydrocarbyl groups of from 1 to about 16 carbon atoms. Similar formulas can be drawn for the phosphonium and sulfonium salts.

The neutralizing anion portion of the salt, i.e. $A^-$ in the above generic formula, may be varied to convenience. Chloride and bromide are the preferred anions, but other representative anions include fluoride, iodide, tosylate, acetate, bisulfate, etc. The following compounds are illustrative: tetraalkylammonium salts, such as tetramethyl-, tetraethyl-, tetrabutyl-, tetrahexyl-, methyltriethyl-, and trioctylmethyl-, hexadecyltriethyl-, and tridecylmethylammonium chlorides, bromides, iodides, bisulfates, tosylates, etc; arylalkylammonium salts, such as tetrabenzylammonium chloride, benzyltrimethyl-, benzyltriethyl-, benzyltributyl-, and phenethyltrimethylammonium chlorides, bromides, iodides, etc; arylammonium salts, such as triphenylmethylammonium fluoride, chloride or bromide, N,N,N-trimethylanilinium chloride, N,N,N-triethylanilinium bromide, N,N-diethyl-N-ethylanilinium bisulfate, trimethylnaphthylammonium chloride, p-methylphenyltrimethylammonium chloride or tosylate, etc.; 5- and 6-membered heterocyclic compounds containing at least one quaternary nitrogen atom in the ring, such as N,N,N',N'-tetramethylpiperaziniumdichloride, N-methylpiperaziniumdichloride, N-hexylpiperazinium iodide, 4-pyridyltrimethylammonium iodide, 1-methyl-1-azonia-bicyclo (2,2,1) heptane bromide, N,N-dibutylmorpholinium chloride, N-ethylthiazolium chloride, N-butylpyrrolium chloride, etc., and the corresponding phosphonium and sulfonium salts.

The 1,3-dihalopropane and the alkali metal cyanide can be used in any suitable ratio to achieve the desired product. Although equimolar amounts can be used, it is generally preferred to have an excess of the 1,3-dihalopropane because one of the features of the invention is to minimize dinitrile formation. Thus, the mole ratio of 1,3-dihalopropane to alkali metal cyanide should be at least about 1.1 to 1 and preferably at least about 1.3 to 1. As an upper limit, a mole ratio of about 3 to 1 and preferably 1.5 to 1 can be employed.

Likewise, the alkali metal halide can be used in any suitable amount. In general, the mole ratio of the alkali metal halide to the 1,3-dihalopropane can be at least about 0.3 to 1 and preferably at least about 0.8 to 1. As an upper limit, a mole ratio of about 3 to 1 and preferably about 1.2 to 1 can be employed.

The amount of the onium salt required is a catalytic amount. This amount is at least about 0.25 percent by weight based on the weight of the reactants with a preferred lower limit of about 1 percent. There is no theoretical upper limit but practical problems of solubility and separation indicate that the catalyst should not exceed about 10 weight percent, with a preferred upper limit of about 5 weight percent.

The temperature and pressure at which the process is conducted is not critical and thus can be selected as desired. By way of illustration, the process can be conducted at autogenous pressure and at a temperature at which the reaction mass is a liquid. It is generally preferred that the process be conducted at a temperature of at least about 50°C, with an upper limit of about 105°C, since best yields are thus obtained.

As previously stated, the process is practiced in the presence of sufficient water to dissolve the inorganic salts. Organic solvents, although unnecessary, may be used if desired. The organic solvents may range from aqueous solutions containing minor amounts of methanol, ethanol, propanol, and the like, to water immiscible organic solvents, i.e., benzene, chlorobenzene, o-dichlorobenzene and the like.

The following examples are illustrative of certain specific embodiments of the invention. However, these examples are for illustrative purposes only and should not be construed as limitations upon the invention.

SPECIFIC EMBODIMENTS

EXAMPLE 1

157.5 g of 1-chloro-3-bromopropane, 29.4 g of sodium cyanide in the form of a 33 percent aqueous solution, 58.5 g of sodium chloride, and 3 g of benzyltriethylammonium chloride (BTEAC) were added to a 1-liter flask. Sufficient water was then added to the 1-liter flask to dissolve all the inorganic salts. The resulting solution was then refluxed at 96°C with vigorous agitation for 4 hours. The organic phase was then separated. Unreacted 1-chloro-3-bromopropane was removed by distillation leaving an orange-colored liquid residue weighing 59.3 g. Analysis of said residue by gas chromatography gave the following composition:

$ClCH_2CH_2CH_2CN$ - 90 percent
$BrCH_2CH_2CH_2CN$ - 7 percent
$NCCH_2CH_2CH_2CN$ - 3 percent Based on theoretical cyanide, the yield was better than 98 percent.

CONTROL A

γ-chlorobutylnitrile was prepared by following the prior art procedure. 157.5 g of 1-chloro-3-bromopropane and 133 g of absolute ethanol were added to a 2-liter flask. The resulting solution was heated to 50°–55°C and 29.4 g of sodium cyanide in the form of a 33 percent aqueous solution was added slowly with stirring over 40 minutes. For an additional hour the reaction was stirred at 50°–55°C and then 133 g of water was added. The ethanol-water solution was distilled until a phase separation occurred. To enhance phase separation, 20 g of calcium chloride was added and the mixture was cooled to 45°C. The organic phase was then separated as 50 g of an orange-brown oil. The oil was analyzed by gas chromatography and was found to have the following composition:

$ClCH_2CH_2CH_2CN$ - 80 percent
$BrCH_2CH_2CH_2CN$ - 14 percent
$NCCH_2CH_2CH_2CN$ - 6 percent Based upon theoretical cyanide, the yield was only 63 percent, 35 percent less than Example 1.

CONTROL B

Example 1 was repeated but without the use of an alkali metal halide. The cyanide consumption was essentially quantitative but the product distribution was as follows:

$ClCH_2CH_2CH_2CN$ - 55 percent
$BrCH_2CH_2CH_2CN$ - 30 percent
$NCCH_2CH_2CH_2CN$ - 15 percent The higher percentage of the dinitrile compound which is nonuseful in the production of cyclopropylcyanide indicates the need for the presence of the alkali metal halide.

CONTROL C

Example 1 was repeated except that neither alkali metal halide nor any water was present. The reaction temperature was held at 90°C with stirring for 3 hours at the end of which time the organic phase consisted of:

$ClCH_2CH_2CH_2Br$ - 50 percent
$ClCH_2CH_2CH_2Cl$ - 25 percent
$BrCH_2CH_2CH_2Br$ - 25 percent Only a trace of cyanide was incorporated. This is indicative that it is necessary to have water present as an exchange medium for the anions associated with the onium salt catalysts.

CONTROL D

Example 1 was repeated but without BTEAC. At the end of 4 hours only 15 percent of the theoretical cyanide incorporation had occurred. This is indicative that the onium salt serves as a catalyst in the process.

EXAMPLE 2

The process of Example 1 was repeated except that 103 g of sodium bromide was substituted for the 58.5 g of sodium chloride. The conversion was 92 percent and the product distribution was:

$ClCH_2CH_2CH_2CN$ - 48 percent
$BrCH_2CH_2CH_2CN$ - 48 percent
$NCCH_2CH_2CH_2CN$ - 4 percent

EXAMPLE 3

Example 1 is repeated except that benzyltriphenylphosphonium chloride is substituted for BTEAC to obtain both a similarly high conversion of theoretical cyanide and high yield of γ-halobutylnitriles.

EXAMPLE 4

Example 1 is repeated except that triphenylsulfonium chloride is substituted for BTEAC to obtain both a similarly high conversion of theoretical cyanide and high yield of γ-halobutylnitrile.

While the invention has been described with specific reference to particular embodiments, it is to be understood that it is not to be limited thereto but is to be construed broadly and restricted solely by the scope of the appended claims.

What is claimed is:

1. A process for the preparation of γ-halonitriles comprising reacting by contacting a 1,3-dihalopropane wherein the halogens are chlorine, bromine, or iodine, with an alkali metal cyanide in the presence of at least 0.3 moles of an alkali metal halide wherein the halide is chlorine, bromine, or iodine, per mole of the 1,3-dihalopropane, sufficient water to dissolve the inorganic salts, and a catalytic amount of an onium salt selected from the group consisting of a quaternary ammonium salt, a quaternary phosphonium salt, and a tertiary sulfonium salt.

2. The process of claim 1 wherein the 1,3-dihalopropane is 1-chloro-3-bromopropane.

3. The process of claim 1 wherein the alkali metal cyanide is sodium or potassium cyanide.

4. The process of claim 1 wherein the alkali metal halide is sodium or potassium chloride.

5. The process of claim 1 wherein the onium salt catalyst is benzyltriethylammonium chloride.

6. The process of claim 1 wherein the mole ratio of 1,3-dihalopropane to alkali metal cyanide is between about 1.1 to 1 and about 3 to 1.

7. The process of claim 1 wherein the mole ratio of 1,3-dihalopropane to alkali metal cyanide is between about 1.3 to 1 and about 1.5 to 1.

8. The process of claim 1 wherein the mole ratio of alkali metal halide to 1,3-dihalopropane is between about 0.3 to 1 and about 3 to 1.

9. The process of claim 1 wherein the mole ratio of alkali metal halide to 1,3-dihalopropane is between about 0.8 to 1 and about 1.2 to 1.

10. The process of claim 1 wherein the onium salt catalyst is present in an amount from about 0.25 to about 10 weight percent based on the total weight of the reactants.

11. The process of claim 1 wherein the onium salt catalyst is present in an amount from about 1 to about 5 weight percent based on the total weight of the reactants.

12. The process of claim 1 wherein the contacting is conducted at a temperature of between about 50°C and about 105°C.

13. The process of claim 1 wherein the contacting is conducted at an autogenous pressure.

14. The process of claim 1 wherein the contacting is conducted in the absence of an organic solvent.

* * * * *